(12) United States Patent
Barnea et al.

(10) Patent No.: US 7,678,582 B2
(45) Date of Patent: Mar. 16, 2010

(54) ASSAYS FOR PREIMPLANTATION FACTOR AND PREIMPLANTATION FACTOR PEPTIDES

(75) Inventors: Eytan R. Barnea, Cherry Hill, NJ (US); Ruben Rene Gonzalez Perez, Watertown, MA (US); Paul C. Leavis, Epping, NH (US)

(73) Assignee: BioIncept, LLC, Cherry Hill, NJ (US)

( * ) Notice: Subject to any disclaimer, the term of this patent is extended or adjusted under 35 U.S.C. 154(b) by 76 days.

(21) Appl. No.: 11/855,519

(22) Filed: Sep. 14, 2007

(65) Prior Publication Data
US 2008/0299677 A1 Dec. 4, 2008

Related U.S. Application Data

(62) Division of application No. 10/482,244, filed as application No. PCT/US02/20599 on Jun. 28, 2002, now Pat. No. 7,273,708.

(60) Provisional application No. 60/302,607, filed on Jul. 2, 2001.

(51) Int. Cl.
*G01N 33/53* (2006.01)
(52) U.S. Cl. ....................... 436/510; 435/7.1
(58) Field of Classification Search ............ None
See application file for complete search history.

(56) References Cited

U.S. PATENT DOCUMENTS

| | | | |
|---|---|---|---|
| 5,646,003 A | 7/1997 | Barnea et al. | |
| 5,981,198 A | 11/1999 | Barnea et al. | |
| 6,171,591 B1 | 1/2001 | Hall | |
| 7,273,708 B2 | 9/2007 | Barnea et al. | |
| 2002/0004205 A1 | 1/2002 | Consler et al. | |
| 2005/0064520 A1 | 3/2005 | Barnea et al. | |

FOREIGN PATENT DOCUMENTS

| | | |
|---|---|---|
| WO | WO 94/06464 A | 3/1994 |
| WO | WO 03/004601 | 1/2003 |
| WO | WO 2004/053086 | 6/2004 |
| WO | WO 2005/040196 | 5/2005 |
| WO | WO 2005/040196 A2 | 5/2005 |
| WO | WO 2006/113898 A2 | 10/2006 |

OTHER PUBLICATIONS

Boklage, Survival probability of human conceptions from fertilization to term, 1990, Int. J. Fert. 35:75.
Navot et al., Poor oocyte quality rather than implantation failure as a cause of age-related decline female fertility, 1991, Lancet 337:1375-1377.
Gardner et al., Complex physiologically based serum-free culture media increase mammalian embryo development, 1997, In vitro fertilization and assisted reproduction, Gomel et al., eds., 10th World Congress, p. 187.
Roussev et al., A novel bioassay for detection of preimplantation factor (PIF), 1995, Am. J. Reproductive Immunology and Microbiology 33(1):68-73.
Gonzalez et al., Preimplantation factor (PIF) may modulate maternal cellular immunity (CD2), 2001, Am. J. Reproduction Immunology 46(1):68-69.
Roussev et al., Development and Validation of an Assay for Measuring Preimplantation Factor (PIF) of Embryonal Origin, 1996, Am. J. Reproduction Immunology 35:281-287.
Barnea et al., Implantation, in Obstetrics & Gynecology, Section 2 Human Re production—Anatomy, Physiology, Embryology, Munteanu Ed. (Romanian Academy of Science Publishers), pp. 117-123 (TOC only), 2001.
Barnea et al., Evolution of the feto-placental unit, in Obstetrics & Gynecology, Section 2 Human Re production—Anatomy, Physiology, Embryology, Munteanu Ed. (Romanian Academy of Science Publishers), pp. 170-175, 2001.
Barnea, 2000, Embryo-Maternal dialogue: linking pregnancy recognition to proliferation control, Rochester Trophoblast Conference 2000, under the auspices of the Trophoblast Conference and SIEP, the Society for the Investigation of Early Pregnancy, Rochester, NY.
Gonzalez et al., Immunomodulatory features of preimplantation factors (PIF) from mouse embryos, 11th World Congress on Human Reproduction Jun. 1-4, 2002, Montreal, Canada (Abstract).
Barnea, The role of preimplantation factor (PIF) in the immune response of pregnancy, Second International Congress on Autoimmunity, Mar. 1999, Tel Aviv, Israel.
Barnea, Embryo-Maternal dialogue, pregnancy recognition and development of immune tolerance, Fourth World Conference on Early Pregnancy: Continuum between implantation and Perinatal Events, under the auspices of the Hungarian Society of Obstetrics and Gynecology and SIEP, the Society for the Investigation of Early Pregnancy, Pecs, Hungary, 2000.
Barnea et al., Progress in characterization of preimplantation factor (PIF) in embryo cultures and in vivo, 1999, Am. J. Reprod. Immunol. 42(2):95-99.

(Continued)

*Primary Examiner*—Jacob Cheu
(74) *Attorney, Agent, or Firm*—Pepper Hamilton LLP

(57) ABSTRACT

The present invention relates to assay methods used for detecting the presence of PIF, and to PIF peptides identified using this assay. In particular, the present invention relates to flow cytometry assays for detecting PIF. It is based, at least in part, on the observation that flow cytometry using fluorescently labeled anti-lymphocyte and anti-platelet antibodies demonstrated an increase in rosette formation in the presence of PIF. It is further based on the observation that flow cytometry demonstrated that monoclonal antibody binding to CD2 decreased in the presence of PIF. The present invention further relates to PIF peptides which, when added to Jurkat cell cultures, have been observed to either (i) decrease binding of anti-CD2 antibody to Jurkat cells; (ii) increase expression of CD2 in Jurkat cells; or (iii) decrease Jurkat cell viability. In additional embodiments, the present invention provides for ELISA assays which detect PIF by determining the effect of a test sample on the binding of anti-CD2 antibody to a CD2 substrate.

1 Claim, 8 Drawing Sheets

OTHER PUBLICATIONS

Barnea, 1997, Editorial: The Embryo: a privileged entity in a privileged site: Lessons learnt from embryonal development, Early Pregnancy: Biol. & Med., 3:77-80.

Barnea, 2000, Editorial: Current progress in Early Pregnancy investigation and the steps ahead Part I, Early Pregnancy Biology & Medicine, 4:104, 4:1-4 (SIEP Publ @ www.earlypregnancy.org).

Barnea et al., Embryo-maternal signaling prior to implantation, in Obstetrics & Gynecology, Section 2 Human Reproduction—Anatomy, Physiology, Embryology, Munteanu Ed. (Romanian Academy of Science Publishers), pp. 112-117, 2001.

Roussev et al., Embryonic origin of preimplantation factor (PIF): biological activity and partial characterization, 1996, Mol. Human Reprod., 2:883-887.

Barnea, Editorial: EnVision the field of Early Pregnancy Investigation, Early Pregnancy, 1995, Biol. & Med., 1:169-170.

Rayburn, Embryonic Medicine and Therapy, (Jauniaux, E., Barnea, E.R., Edwards, R.G., eds.) The New England Journal of Medicine Book Review, 340(19):1519, 1999.

Barnea, Keynote Editorial: New Frontiers in Early Pregnancy Investigation, Early Pregnancy, 1995, Biol. & Med., 1:1-3.

Barnea et al., Editorial: Reflections on early pregnancy: organizing chaos or organized chaos?, Early Pregnancy, 1996, Biol. & Med., 2:77-79.

Barnea et al., Use of lymphocyte platelet binding assay for detecting a preimplantation factor: A quantitative assay, 1994, Am. J. Reprod. Immunol. 32:133-138.

Barnea, Immune system and proliferation control evolution from embryo to adulthood: Roles of preimplantation factor (PIF)* and development proteins (DPs), Renaissance Congress of the 21$^{st}$ Century: The Mother and Child, before, during and after pregnancy, A Global union of Scientific Congresses, under the high patronage of the President of the Italian Republic, 5$^{th}$ SIEP World Conference, 1$^{st}$ International Congress of the Mediterranean Society of Reproduction and Neonatology, 4$^{th}$ International Congress of the International Society for New Technology in Gynecology, Reproduction and Neonatology, Rome, Italy, 2001.

Coulam et al., Preimplantation factor (PIF) predicts subsequent pregnancy loss, 1995, Am. J. Reprod. Immunol. 34:88-92.

Barnea et al., Embryonic Signals, in Jauniaux, E., Barnea, E.R., Edwards, R.G. (eds.) Embryonic Medicine and Therapy, pp. 63-75 (Oxford University Press), 1997.

Barnea, 2001, Underlying mechanisms and treatment of early pregnancy failure, Ferti Magazine, Ferti.Net Worldwide Fertility Network.

Mirhashemi, Cancer and Pregnancy, (Barnea, E.R., Jauniaux, E., Schwartz, P.E., eds.) The New England Journal of Medicine Book Review, 346(46):1921, 2002.

Barnea et al., Maternal Immune Response to Trophoblast, GTD and Cancer, In: Shoenfeld, Y. and Gerhwin, M.E. (eds) Cancer and Autoimmunity, pp. 343-350, Elsevier Science B.V. Publishers, 2000.

Barnea et al., Identification and validation of an assay for preimplantation (PIF). Society for Gynecological Investigation 41$^{st}$ Meeting, April, Chicago, IL (Abstract), 1994.

Roussev et al., Clinical validation of preimplantation factor (PIF) assay, Second World Conference on Preimplantation and Early Pregnancy in Humans, May, Atlantic City, NJ (Abstract), 1994.

Roussev et al., A novel bioassay for detection of preimplantation factor (PIF), American Society of Reproductive Immunology, XVI Annual Meeting, June, Philadelphia, PA (Abstract), 1994.

Coulam et al., Preimplantation factor (PIF) predicts subsequence pregnancy loss, The American Fertility Society 50$^{th}$ Annual Meeting, November, San Antonio, TX (Abstract), 1994.

Roussev et al., Embryonic origin of preimplantation factor (PIF), Society for Gynecological Investigation 42$^{nd}$ Meeting, Chicago, IL (Abstract), 1995.

Barnea et al., Partial characterization of embryo-derived preimplantation factor (PIF), Ninth World Congress on Human Reproduction, May, Philadelphia, PA (Abstract), 1996.

Barnea et al., Preimplantation factor (PIF): current developments, Third World Conference on Early Pregnancy—An Interdisciplinary Approach, October, Atlantic City, NJ (Abstract), 1996.

Barnea et al., Partial characterization of mammalian preimplantation factor (PIF) in culture and in vivo, Fourth International Meeting Mechanisms in Local Immunity: and join meeting Fourth Meeting of Alps Adria Society for Immunology of Reproduction (AASIR), September, Opatija, Croatia (Abstract), 1998.

Barnea, Preimplantation Factor: A specific embryo viability factor, The First National Congress on Human Assisted Reproduction with International Participation under the patronage of the Romanian Academy, Timisoara, Romania (Abstract), 1999.

Gonzales et al., Preimplantation factor (PIF) could be a portion of CD2 or a homologue peptide, 57$^{th}$ Annual Meeting of the American Society for Reproductive Medicine, Orlando, FL (Abstract), 2001.

Barnea, Safeguards established at conception influence peri and postnatal life: Roles of Preimplantation Factor (PIF) and Developmental Proteins (DPs), World Congress of Perinatal Medicine, Parallel Scientific SIEP Meeting, Barcelona, Spain (Abstract), 2001.

Barnea, Novel Preimplantation Factors (PIF) and Developmental Peptides (DPs) are involved in safeguarding pregnancy, The Fetus as a Patient, Budapest, Hungary (Abstract), 2002.

Gonzales et al., Preimplantation factors (PIF) embryo-derived immunomodulatory peptides: possible implications for maternal recognition and allograft tolerance, 22$^{nd}$ Annual Meeting of the American Society for Reproductive Immunology, Chicago, IL (Abstract), 2002.

Paidas et al., Pregnancy Implantation Factor (PIF) activity is correlated with a pro-inflammatory response, 23$^{rd}$ Annual Society for Maternal-Fetal Medicine Conference, San Francisco, CA (Abstract), 2002.

Barnea et al., Further validation of an assay for preimplantation factor (PIF), Second World Conference on Preimplantation and Early Pregnancy in Humans, May, Atlantic City, NJ (Abstract), 1994.

Gonzales et al., Preimplantation factor (PIF) may modulate maternal cellular immunity (CD2), VII International Congress of Reproductive Immunology, Organized by ISIR, The International Society for Immunology of Reproduction, Opatja, Croatia, 2001.

Raghupathy, Th 1-type immunity is incompatible with successful pregnancy, 1997, Today 18(10):478-482.

Wegmann et al., Bidirectional cytokine interactions in the maternal-fetal relationship: is successful pregnancy a $T_H2$ phenomenon? 1993, Immunol. Today 14(7):353-356 (Abstract).

Cavanagh, et al., The purification of early-pregnancy factor to homogeneity from human platelets and identification as chaperonin 10, 1994, Eur. J. Biochem. 222:551-560.

Piccinni et al., Production of IL-4 and leukemia inhibitory factor by T cells of the cumulus oophorus: a favorable microenvironment for pre-implantation embryo development, 2001, Eur. J. Immunol. 8:2431-2437.

Wickramasinghe et al., Blood and bone marrow changes in malaria, 2000, Best Pract. Res. Clin. Haematol. 13:277-299.

Romagnani, Lymphokine production by human T cells in disease states, 1994, Ann. Rev. Immunol. 12:227-257.

Chaouat et al., IL-10 prevents naturally occurring fetal loss in the CBA × DBA/2 mating combination, and local defect in IL-10 production in this abortion-prone combination is corrected by in vivo injection of IFN-tau, 1995, Immunol. 154:4261-4268 (Abstract).

Ho et al., Distribution of Th1 and Th2 cell populations in human peripheral and decidual T cells from normal and and embryonic pregnancies, 2001, Fertil. Steril. 76(4):797-803.

Wu et al., Increase in the production of interleukin-10 early after implantation is related to the success of pregnancy, 2001, Am. J. Reprod. Immunol. 46(6):386-392.

Choudhury et al., Human reproductive failure I: Immunological factors, 2001, Hum. Reprod. Update 7(2)113-134.

Heyner, Growth factors in preimplantation development: role of insulin and insulin-like growth factors, 1997, Early Preg. Biol. and Med. 3:153-163.

Abbas et al., Functional diversity of helper T lymphocytes, 1996, Nature 383:787-793.

Taubes, Malaria Parasite Outwits the Immune System, 2000, Science 290:435.

Medrano et al., Sequence analysis of the polymerase domain of HIV-1 reverse transcriptase in naïve and zidovudine-treated individuals reveals a higher polymorphism in alpha-helices as compared with beta-strands, 1999, Virus Genes 18(3):203-210.

Chen et al., Preimplantation Factors (PIF) Embryo-Derived Immunomodulatory Peptides: Possible Implications for Maternal Recognition and Allograft Tolerance, 2002, Am. Soc. for Reproduction Immunology 47(6):347.

Bodian et al., Crystal Structure of the Extracellular Region of the Human Cell Adhesion Molecule CD2 at 2.5 A Resolution, Laboratory of Molecular Biophysics, Oxford, UK, Structure, Aug. 15, 1994, vol. 2(8):755-766 (Abstract).

Critser et al., The Role of Platelet-Activating Factor in Reproduction, Chapter 15 in Immunological Obstetrics, W.W. Norton, New York, 1992, pp. 202-215.

Fiocchi et al., Intestinal Inflammation: a complex interplay of immune and nonimmune cell interactions, 1997, Am. J. Physiol. Gastrointest. Liver Physiol. 273:G769-G775.

Morgan et al., Approaches to the Discovery of Non-Peptide Ligands for Peptide Receptors and Peptidases, 1989, Annual Reports in Medicinal Chemistry 24: 243-252.

Goodman et al., The Pharmacological Basis of Therapeutics, $6^{th}$ ed., MacMillan Publ. Co., New York, 1980 (TOC).

Banker et al., Modern Pharmaceutics, Marcel Dekker, Inc., New York, 1979 (TOC).

Ripka et al., Peptidomimetic design, 1998, Curr. Op. Chem. Biol. 2:441-452.

Gardner et al., Culture of viable human blastocysts in defined sequential serum-free media, 1998, Hum. Reprod. Suppl 3:148-160.

Barnea, Insight into early pregnancy: emerging role of the embryo, 2004, Am. J. Reprod. Immunol. 51:319-322.

Fuzzi et al., HLA-G expression in early embryos is a fundamental prerequisite for the obtainment of pregnancy, 2002, Eur. J. Immunol. 32:311-315.

Bainbridge et al., HLA-G remains a mystery, 2001, Trends Immunol. 22:548-552.

Rogers et al., Maternal-fetal tolerance is maintained despite transgene-driven trophoblast expression of MHC class I, and defects in Fas and its ligand, 1998, Eur. J. Immunol. 28:3479-3487.

Guller et al., The role of placental Fas ligand in maintaining immune privilege at maternal-fetal interfaces, 1999, Semin. Reprod. Endocrinol. 17:39-44.

Mattson et al., Placental MCH class I antigen expression is induced in mice following in vivo treatment with recombinant interferon gamma, 1991, J. Reprod. Immunol. 19:115-129.

Zhou et al., Expanded cohorts of maternal CD8+T-cells specific for paternal MCH class I accumulate during pregnancy, 1998, J. Reprod. Immunol. 40:47-62.

Mellor et al., Extinguishing maternal immune responses during pregnancy: implications for immunosuppression, 2001. Semin. Immunol. 13:213-218.

Szekeres-Bartha, Immunological relationship between the mother and the fetus, 2002, Int. Rev. Immunol. 21:471-495.

Loke et al., Immunology of implantation, Ballieres Best Pract. Obstet. Gynecol. 2000, 14:827-837.

Aplin et al., Trophoblast-uterine interaction at implantation, 2004, Reprod. Biol. and Endocrinol. , Doi 10.1-1186/1477-7827-2-48.

Somerset et al., Normal human pregnancy is associated with an elevation in the human suppressive CD25+CD4+ regulatory T-cell subset, 2004, Immunology 112:38-43.

Fortin et al., TGF-beta and PGE2 in rabbit blastocoelic fluid can modulate GM-CSF production by human lymphocytes, 1997, Am. J. Reprod. Immunol. 38:129-139.

Pinkas et al., Immunesuppressive activity in culture media containing oocytes fertilized in vitro, 1992, Arch. Androl. 28:53-59.

Minhas et al., Platelet activating factor and conception, 1996, Am. J. Reprod. Immunol. 35:267-271.

Sipka et al., Glucocorticosteroid dependent decrease in the activity of calcineurin in the peripheral blood mononuclear cells of patients with systemic lupus erythematosus, 2001, Ann. Rheum. Dis. 60:380-384.

Rolfe et al., Cyclosporin A and FK506 reduce interleukin-5 mRNA abundance by inhibiting gene transcription, 1997, Am. J. Reprod. Cell. Mol. Biol. 17:243-250.

Moffett-King, Natural killer cells and pregnancy, 2002, Nat. Rev. Immunol. 2:656-663.

Rosario et al., Morphological events in the primate endometrium in the presence of a preimplantation embryo, detected by the serum preimplantation assay, 2005, Hum. Reprod. 20:61-71.

Bates et al., Aberrant cytokine production by peripheral blood mononuclear cells in recurrent pregnancy loss, 2002, Human Reprod. 17:2439-2444.

Raghupathy, Pregnancy success and failure within the Th1/Th2/Th3 paradigm, 2001, Semin. in Immunol. 13:219-227.

Chaouat et al., TH1/TH2 paradigm in pregnancy: paradigm lost? Cytokines in pregnancy/early abortion re-examining the Th1 and Th2 paradigm, 2004, Int. Arch. Aller. Immunol., 134:93-109.

Mocellin et al., The dual role of IL-10, 2003, Trends in Immunol. 24:36-43.

McGuirk et al., Pathogen-specific regulatory T cells provoke a shift in the Th1/ and Th2 paradigm in immunity to infectious diseases, 2002, Trends in Immunol. 23:450-455.

Liu, The yins of T cells activation, 2005, Sci STKE 265.

Diouf et al., Monocyte activation and T cell inhibition in plasmodium falciparum infected placenta, 2004, J. Infect. Dis. 189:2235-2242.

Ancsin et al., A binding site for highly sulfated heparin sulphate is identified in the N terminus of the circumsporozoite protein, 2004, J. Biol. Chem. 279:21824-21832.

Hardy et al., Growth factor expression and function in the human and mouse preimplantation embryo, 2002, J. Endocrinol. 172:221-236.

Jiang et al., Cutting Edge: Multiple mechanisms of peripheral T cell tolerance to the fetal "allograft", 1998, J. Immunol. 160:3086-3090.

Rieger et al., Th1 and Th2-like cytokine production by first trimester decidual large granular lymphocytes is influenced by HLA-G and HLA-E, 2002, Mol. Hum. Reprod. 8:255-261.

Runmarker et al., Pregnancy is associated with a lower risk of onset and better diagnosis in multiple sclerosis, 1995, Brain 188(part 1):253-261.

Kaaja et al., Manifestations of chronic disease during pregnancy, 2005, JAMA 21:2751-2757.

Resnick et al., Nonmyeloablative stem cell transplantation and cell therapy for malignant and non-malignant diseases, 2005, Transpl. Immunol. 14:207-219.

Slavin et al., Non-myeloablative stem cell transplantation for the treatment of cancer and life-threatening non-malignant disorders; past accomplishments and future goals, 2002, Transfus. Apher. Sci. 27:159-166.

Ferrara et al., Acute graft versus host disease: pathophysiology, risk factors, and prevention strategies, 2005, Clin. Adv. Hematol. Oncol. 3:415-419.

Or et al., The prophylactic potential of fludarabine monophosphate in graft-versus-host disease after bone marrow transplantation in murine models, 2000, Bone Marrow Transplantation 25:263-266.

Elad et al., Budesonide: A novel treatment for oral chronic graft-versus-host disease, 2003, Oral Surg. Oral Med. Oral Pathol. Oral Radiol. Endod. 95:308-311.

Slavin et al., The graft-versus-leukemia (GVL) phenomenon: is GVL separable from GVHD?, 1990, Bone Marrow Transplant. 6:155-161.

Truitt, The Mortimer M. Bortin Lecture: To destroy by the reaction of immunity: the search for separation of graft-versus-leukemia and graft-versus-host, 2004, Biol. Blood Marrow Transplant 10:505-523.

Mielcarek et al., Graft-vs-host disease after non-myeloablative hematopoietic cell transplantation, 2005, Leuk. Lymphona 46:1251-1260.

Lederman et al., Defective suppressor cell generation in juvenile onset diabetes, 1981, J. Immunol. 127:2051-2055.

Asano et al., Autoimmune disease as a consequence of developmental abnormality of a T cell subpopulation, 1996, J. Exp. Med. 184:387-396.

Salomon et al., B7/CD28 costimulation is essential for the homeostasis of the CD4+CD25+ immunoregulatory T cells that control autoimmune diabetes, 2000, Immunity, 12:431-440.

Bresson et al., Mechanisms underlying type I diabetes, 2004, Drug Discovery Today: Disease Mechanisms 1:321-327.

Herold et al., Anti-CD3 monoclonal antibody in new-onset type 1 diabetes mellitus, 2002, N. Engl. J. Med. 346:1692-1698.

Eisenbarth et al., Anti-thymocyte globulin and prednisone immunotherapy of recent onset type 1 diabetes mellitus, 1985, Diabetes Res. 2:271-276.

Raz et al., β-cell function in new-onset type 1 diabetes and immunomodulation with heat-shock protein peptide (DialPrep277): a randomized, double-blind, phase II trial, 2001, Lancet 358:1749-1753.

Atkinson et al., The NOD mouse model of T1D: as good as it gets?, 1999, Nat. Med. 5:601-604.

Wu et al., Tumor necrosis factor-alpha regulation of CD4+CD25+ T cell levels in NOD mice, 2002, Proc. natl. Acad. Sci. USA 99:12287-12292.

Weiss et al., Induction of resistance to diabetes in non-obese diabetic mice by targeting CD44 with a specific monoclonal antibody, 2000, PNAS 97:285-290.

Elkin et al., Prevention of diabetes in nonobese diabetic mice by non-myeloablative a llogenic bone marrow transplantation, 2004, Exp. Hematol. 32:579-584.

McFarland, Correlation between MR and clinical findings of disease activity in multiple sclerosis, 1999, Am. J. Neuro. Radiol. 20:1777-1778.

Hafler, Multiple Sclerosis, 2004, J. Clin. Invest. 113:788-794.

Dyement et al., Genetics of multiple sclerosis, 2004, Lancet Neurol. 3:104-110.

Johnson et al., Copolymer 1 reduces relapse rate and improves disability in relapsing-remitting multiple sclerosis: results of phase III multicenter, double-blind placebo-controlled trial, 1995, Neurology 45:1268-1276.

Sturzebecher et al., Expression profiling identifies responder and non-responder phenotupes to interferon-betha in multiple sclerosis, 2003, Brain 126:1419-1429.

Miller et al., A controlled trial of natalizumab for relapsing multiple sclerosis, 2003, N. Engl. J. Med. 348:15-23.

Burt et al., Hematopoietic stem cell transplantation for progressive multiple sclerosis: failure of a total body irradiation-based conditioning regimen to prevent disease progression in patients with high disability scores, 2003, Blood 102:2373-2378.

Karussis et al., Inhibition of acute, experimental autoimmune encephalomyelitis by the synthetic immunomodulator linomide, 1993, Ann. Neurol. 34:654-660.

Sospedra et al., Immunology of multiple sclerosis, 2005, Ann.. Rev. Immunol. 23:683-747.

Dinh et al., The epidemiology of cancer in pregnancy, 2006, In Cancer and Pregnancy, Barnea et al. eds., Springer, London, 2001, 1:1-6.

Barnea et al., Pregnancy derived compounds that control proliferation, 2001, in Cancer and Pregnancy, Barnea et al. eds., Springer 2:277-286.

Ordentlich et al., Unique forms of human and mouse nuclear receptor corepressor SMRT, 1999, Natl. Acad. Sci. U.S.A. 96:2639-2644.

Park et al., SMRTe, a silencing mediator for retinoid and thyroid hormone receptors-extended isoform that is more related to the nuclear receptor corepressor, 1999, Proc. Natl. Acad. Sci. U.S. A. 96:3519-3524.

Chen et al., A transcriptional co-repressor that interacts with nuclear hormone receptors, 1995, Nature 377:454-457.

Sande et al., Identification of TRACS (T3 receptor-associating cofactors), a family of cofactors that associate with, and modulate the activity of, nuclear hormone receptors, 1996, Mol. Endocrinol. 10:813-825.

Margolis et al., cDNAs with long CAG trinucleotide repeats from human brain, 1997, Hum. Genet. 100:114-122.

Shi et al., Sharp, an inducible cofactor that integrates nuclear receptor repression and activation, 2001, Genes Dev. 15:1140-1151.

Guenther et al., A core SMRT corepressor complex containing HDAC3 and TBL1, a WD40-repeat protein linked to deafness, 2000, Genes Dev. 14:1048-1057.

Li et al., Both corepressor proteins SMRT and N-CoR exist in large protein complexes containing HDAC3, 2000, EMBO J. 19:4342-4350.

Zhang et al., The N-CoR-HDAC3 nuclear receptor corepressor complex inhibits the JNK pathway through the integral subunit GPS2, 2002, Mol. Cell 9:611-623.

Fischer et al., Isolation and characterization of a novel class II histone deacetulase, HDAC10, 2002, J. Biol. Chem. 277:6656-6666.

Beausoleil et al., Large-scale characterization of HeLa cell nuclear phosphoproteins, 2004, Proc. Natl. Acad. Sci. U.S.A. 101:12130-12135.

Olsen et al., Global, in vivo, and site-specific phosphorylation dynamics in signaling networks, 2006, Cell 127:635-648.

Hruby et al., Synthesis of oligopeptide and peptidomimetic libraries, 1997, Curr. Op. Chem. Biol. 1:114-119.

Hruby et al., Conformational and topographical considerations in designing agonist peptidomimetics from peptide leads, 2000, Curr. Med. Chem. Sept.. 7(9): 945-970.

Nahhas et al., Human Embryonic Origin Early Pregnancy Factor Before and After Implantation, 1990, Am. J. Reprod. Immunol. 22:105-108.

Shurtz-Swirski et al., Human Embryo Modulates Placental Function in the First Trimester. Effects of Neural Tissues upon Chorionic Gonadotropin and Progesterone Secretion, 1991, Placenta 15:521-531.

Shurtz-Swirski et al., In vitro Effect of Anti-Cardiolipin Autoantibodies upon Total and Pulsatile Placental hCG Secretion During Early Pregnancy, 1993, Am. J. Reprod. Immunol. 29:206-210.

Sharma et al., Genes Regulating Implantation and Fetal Development, 2005, Frontiers in Bioscience 1(11):2123-2137.

Barnea, Applying Embryo-Derived Immune Tolerance to the Treatment of Immune Disorders: Role of PIF, Ann. NY Acad. Sci., Sep. 2007, 1110:602-618.

Barnea et al., The Embryo-Trophoblast Paradox, In Embryonic Medicine and Therapy, Jauniaux et al. eds., Oxford University Press, 1997, pp. 256-279.

Barnea et al., Immune System (IS) and Proliferation Control (PC) from Embryo to Adulthood: Roles of Preimplantation Factor (PIF) and of Developmental Proteins (DPs), In The Woman and Child Before, During and After Pregnancy, Cosmi ed., Monduzzi Editore, 2001, pp. 93-102.

Barnea et al., Prediction of Implantation in ART using Molecular Biology in Infertility, Art & Endoscopy, 2004, Allahahbadia et al. eds., Elsevier Publ. pp. 183-194.

Barnea, Signaling Between Embryo and Mother in Early Pregnancy: Basis for Development of Tolerance, Recurrent Pregnancy Loss: Causes, Controversies and Treatment. Series in Maternal-Fetal Medicine, Informa Healthcare, Carp ed., HJA Ed., Taylor and Francis Group publ. 2:15-22, 2007.

Than et al., Embryo-Placento-Maternal Interaction and Biomarkers: From Diagnosis to Therapy, A Workshop Report Trophoblast Research 21:S107-S110, 2007.

Nahhas et al., Early Pregnancy Factor Determination in Pregnant and IVF/ET Patients, and in Human Embryo Cultures, American Fertility Society 15th Ann. Mtg., San Francisco, CA, 1989.

Shurtz-Swirski et al., Anti-Cardiolipin Antibodies Affect Total and Pulsatile Placental HCG Secretion during Early Pregnancy, Israel Conference of Fertility, Tel Aviv, Israel, 1993.

Barnea et al., Embyonic Signals, Sixth International Congress of Reproductive Immunology, Washington, DC, 1995.

Barnea et al., Preimplantation Signalling by the Embryo, Third World Conf, on Early Pregnancy-An Interdisciplinary Approach, Atlantic City, NJ, 1996.

Barnea et al., Immune Modulation, by Embryo-Specific Peptides, Allow for Embryo Tolerance whilst Preserving the Maternal Hosts Ability to Fight Pathogens: Preimplantation Factor (PIF)*. First Brown-Linkoping meeting on Basic and Clinical Aspects of Reproductive Immunology, Providence, RI, 2002.

Barnea, Critical Elements for Early Development and Beyond: Immune Tolerance (PIF) and Proliferation Control (DPs): Sixth World Conference of Early Pregnancy: Workshop on Embryology Early Pregnancy Investigation: Highlights into postnatal life: Pre-Congress: IVth Indian Congress on Endoscopy, Infertility & ART. Organized by SIEP, the Society for the Investigation of Early Pregnancy. Supported by Rotunda the Center for Human Reproduction, Mumbai-India and Mangeshikar Center for Gynaelogical Endoscopic Surgery, Mumbai-India. Mumbai-India, Jodphur, India, 2002.

Barnea, Maternal Immune Recognition of Pregnancy is Initiated by Novel Embryo-Derived Preimplantation Factor (PIF). Invited Speaker. Hippokration Congress on Reproductive Immunology (4th ESRADI C) European Society for Reproductive and Developmental Immunology, Rhodes, Greece, 2003 (Abstract).

Barnea et al., Preimplantation Factor (PIF): Relevance for Human Pregnancy, Invited Speaker. 24th Ann. Mtg. of the American Society for Reproductive Immunology, St. Louis, MO, 2004.

Barnea et al., Expression of Novel Immunomodulators (PIF*) and Proliferation Controllers (DPs) by the Embryo and by the Placenta. Invited Speaker at the 32nd Conference of the European Teratology Society, Thessaloniki, Greece, 2004.

Barnea et al., Embryo-Derived Preimplantation Factor (PIF*): Methods to Assess Embryo Viability towards Successful Pregnancy at the Vth Indian Congress of Gynecologic Endoscopy and ART, Khajuraho, India, 2004.

Barnea et al., Preimplantation Factor: From Embryo Tolerance to Embryo Viability Detection and Treatment of Autoimmune Diseases, Eleventh International Symposium for Immunology of Reproduction. (ISIR) International House of Scientists, Varna, Bulgaria, 2006.

Barnea et al., Preimplantation Factor (PIF): Novel Immunemodulatory Peptide and Expression by Gestational Tissues, 12th International Federation of Placenta Association (IFPA) Meeting, Sep. 6-9, 2006, Kobe, Japan.

Barnea et al., Novel Embryo-Derived Preimplantation Factor (PIF): An Immune-Modulatory Therapy Approach for Immune Disorders, 5th International Congress on Autoimmunity, Sorrento, Italy, 2006.

Paidas et al., Pregnancy Implantation Factor (PIF) Upregulates First Trimester Toll Like Receptor-2, Supporting the Role of PIF as an Embryo Derived Factor Influencing Maternal Innate Immunity, 27th Annual Scientific Meeting of the Society for Maternal-Fetal Medicine, San Francisco, CA 2007.

Barnea, Apply Embryo Derived Tolerance for Managing Reproductive and Immune Disorders: Preimplantation Factor (PIF). 27th Annual Meeting of the American Society for Reproductive Immunology, Toronto, Canada, 2007.

Bringer et al., PIF-1 Improves Graft vs. Host Disease (GVHD) while maintaining Graft vs. Leukemia (GVL) effect after bone marrow transplantation in mice, The 5th Annual Congress of the Federation of the Israel Societies for Experimental Biology, Jan. 28-31, Eilat, Israel, 2008.

Barnea, From PIF identification to clinical applications: Immunemodulatory Embryo-Derived Novel Peptide: True BioMarker Dx and Nontoxic Rx Application, Mining the Plasma Proteone Meeting, Success Stories Session, PepTalk Conf., CHI Cambridge Healthtech Institute: Jan. 7-9, Coronado, San Diego CA.

Database UniProt [Online], Nov. 1, 1999, Reverse transcriptase (Fragment), retrieved from EBI accession No. UNIPROT:Q9WFD3 Database accession No. Q9WFD3.

Database YbuOrit [Online], Nov. 1, 1999, Nuclear receptor corepressor 2 (N-CoR2) (Silencing mediator of retinoic acid and thyroid hormone receptor) (SMRT) (SMRTe) (Thyroid-, retinoic-acid-receptor-associated corepressor) (T3 receptor-associating factor) (TRAC) (CTG repeat protein 26) (SMAP270), retrieved from EBI accession No. UNIPROT:Q9Y618 Database accession No. Q9Y618.

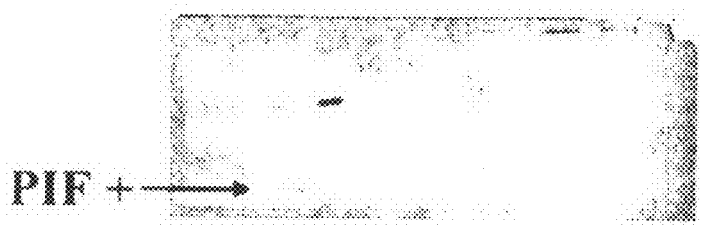
Fig 2A
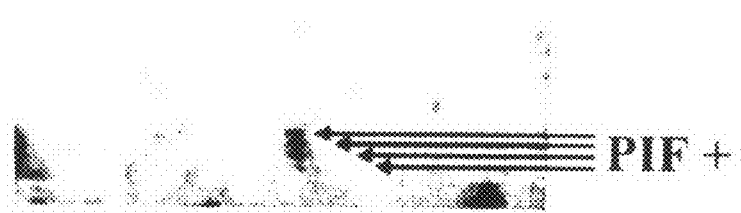
Fig 2B
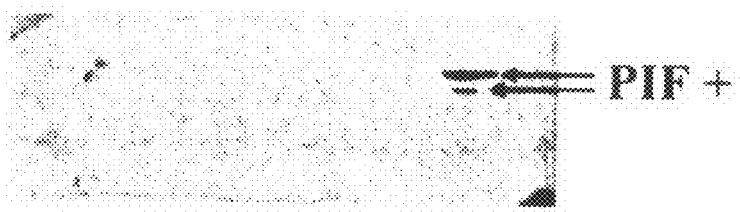
Fig 2C
Fig. 2 ately 73% of natural single conceptions are lost before

SEQUENCE LISTING

```
<160> NUMBER OF SEQ ID NOS: 8

<210> SEQ ID NO 1
<211> LENGTH: 9
<212> TYPE: PRT
<213> ORGANISM: Mus musculus

<400> SEQUENCE: 1

Met Val Arg Ile Lys Pro Gly Ser Ala
 1               5

<210> SEQ ID NO 2
<211> LENGTH: 13
<212> TYPE: PRT
<213> ORGANISM: Mus musculus

<400> SEQUENCE: 2

Met Val Arg Ile Lys Pro Gly Ser Ala Asn Lys Pro Ser
 1               5                  10

<210> SEQ ID NO 3
<211> LENGTH: 14
<212> TYPE: PRT
<213> ORGANISM: Mus musculus

<400> SEQUENCE: 3

Met Val Arg Ile Lys Tyr Gly Ser Tyr Asn Lys Pro Ser Asp
 1               5                  10
```

```
<210> SEQ ID NO 4
<211> LENGTH: 15
<212> TYPE: PRT
<213> ORGANISM: Mus musculus

<400> SEQUENCE: 4

Met Val Arg Ile Lys Pro Gly Ser Ala Asn Lys Pro Ser Asp Asp
1               5                   10                  15

<210> SEQ ID NO 5
<211> LENGTH: 18
<212> TYPE: PRT
<213> ORGANISM: Mus musculus

<400> SEQUENCE: 5

Ser Gly Ile Val Ile Tyr Gln Tyr Met Asp Asp Arg Tyr Val Gly Ser
1               5                   10                  15

Asp Leu

<210> SEQ ID NO 6
<211> LENGTH: 9
<212> TYPE: PRT
<213> ORGANISM: Mus musculus

<400> SEQUENCE: 6

Val Ile Ile Ile Ala Gln Tyr Met Asp
1               5

<210> SEQ ID NO 7
<211> LENGTH: 10
<212> TYPE: PRT
<213> ORGANISM: Mus musculus

<400> SEQUENCE: 7

Ser Gln Ala Val Gln Glu His Ala Ser Thr
1               5                   10

<210> SEQ ID NO 8
<211> LENGTH: 13
<212> TYPE: PRT
<213> ORGANISM: Mus musculus
<220> FEATURE:
<221> NAME/KEY: misc_feature
<222> LOCATION: (12)..(12)
<223> OTHER INFORMATION: Xaa can be any naturally occurring amino acid

<400> SEQUENCE: 8

Ser Gln Ala Val Gln Glu His Ala Ser Thr Asn Xaa Gly
1               5                   10
```

ASSAYS FOR PREIMPLANTATION FACTOR AND PREIMPLANTATION FACTOR PEPTIDES This application claims priority to and is a divisional application of U.S. Non-provisional application Ser. No. 10/482,244 filed Aug. 11, 2004, which is a US National Stage Application under 35 U.S.C. §371 claiming priority to PCT/US2002/20599 filed Jun. 28, 2002, which claims priority to U.S. Provisional Application No. 60/302,607 filed on Jul. 2, 2001.

INTRODUCTION

The present invention relates to preimplantation factor ("PIF") a very early marker of fertilization and embryo viability, to new methods for detecting PIF activity and to PIF peptides.

BACKGROUND OF THE INVENTION

Infertility is a major health care concern affecting millions of couples worldwide. Contributing to this problem, early demise of the human conceptus is a common event. Approximately 73% of natural single conceptions are lost before reaching week 6 of gestation (Boklage C E. Survival probability of human conceptions from fertilization to term. Int J Fertil 1990; 35:75). This is mostly due to early embryonic demise prior to implantation or soon after implantation occurs. Data relating to the low fertility rate observed in older women and its improvement by oocyte donation from young women indicate that oocyte quality is an important factor in achieving a successful pregnancy (Navot D, Bergh P A, Williams M A et al. Poor oocyte quality rather than implantation failure as a cause of age-related decline female fertility. Lancet 1991; 337:1375).

In vitro fertilization ("IVF") is a technology which has been developed to address the problem of infertility. However, maintaining embryo viability is even more problematic under the artificial conditions used for culturing embryos in vitro for implantation. In vitro, the embryo development rate is lower than in vivo and only 25-65% of embryos typically develop to the blastocyst stage (Gardner D K, Lane M, KOuridakis K, Schoolvcraft W B. Complex physiologically based serum-free culture media increase mammalian embryo development. In: Gomel V, Leung P C K, eds. In vitro fertilization and assisted reproduction. Procc 10th World Congress, 1997: 187). The state of the art is not yet able to identifying embryos likely to implant and survive. Human chorionic gonadotrophin ("hCG"), the currently used marker for fertilization in vivo and early embryo implantation, can only be detected several days after implantation. As a result of the lack of a suitable marker for embryo viability, nowadays many embryos incapable of implanting are being transferred, thus lowering the chance for achieving successful pregnancy.

To address the possibility that embryos may not be viable, a greater number of embryos are simultaneously transferred into a potential mother. The transfer of a high number of embryos may lead to multiple pregnancies, which are inherently risky, while transfer of a small number of embryos carries the risk that none would implant, losing a whole IVF cycle. Clearly, there is a need to improve embryo selection and define accurate markers to determine embryo viability. In addition, using non-invasive methods by testing culture media for products specific to viable, implantation-competent embryos would allow selection of those most likely to result in successful pregnancies, without causing embryo damage.

Another factor involved in determining whether a pregnancy is successful or not is the interaction between the conceptus and the mother's immune system. Shortly after fertilization a systemic maternal recognition of pregnancy should occur. The mother's immune system modulation triggered by specific early embryo signals could be the key of this process. Once the oocyte is fertilized, the zygote up to hatching blastocyst is surrounded by the zona pellucida, a hard semi permeable membrane. Therefore the embryo-maternal communication must occur simultaneously while the embryo is developing in the oviduct and uterine cavity through compounds that are secreted by the embryo.

It has been shown that pregnant sera and viable embryo conditioned culture media can produce an increase in rosette formation by platelets and T lymphocytes in the presence of CD2 antibody. As disclosed in U.S. Pat. No. 5,646,003 by Barnea et al., issued Jul. 8, 1997, and in U.S. Pat. No. 5,981,198 by Barnea et al., granted Nov. 9, 1999, the presence of Preimplantation Factor ("PIF") can be detected by mixing lymphocytes, platelets, heat inactivated serum from a pregnant subject, guinea pig complement, and T11 (anti-CD2) monoclonal antibody (Dakko, Denmark), where rosette formation between platelets and lymphocytes is increased by PIF in pregnant subjects. PIF has been found to be (i) secreted by viable early human and mouse embryos from the two-cell stage onward; detectable in the peripheral circulation 3-4 days after embryo transfer following IVF; (iii) associated with 73% take home babies vs 3% in early negative PIF results; (iv) detectable 5-6 days after intrauterine insemination; (v) absent in non-pregnant serum, or non-viable embryos; and (vi) present in various pregnant mammals in addition to humans, including mice, horses, cows and pigs. In addition, PIF has been observed to disappear from the circulation two weeks before hCG secretion declines in cases of spontaneous abortion.

The monoclonal antibody used in the above-mentioned PIF assay is directed toward the lymphocyte associated antigen referred to as CD2. CD2 is present on about 80-90% of human peripheral blood lymphocytes, greater than 95% of thymocytes, all T lymphocytes that form erythrocyte rosettes and a subset of NK cells. Various roles for CD2 in T cell activation have been proposed, including function as an adhesion molecule which reduces the amount of antigen required for T cell activation and as a costimulatory molecule or direct promoter of T cell activation. Moreover, CD2 has been implicated in the induction of anergy, the modulation of cytokine production and the regulation of positive selection of T-cells.

The natural ligand for CD2 is the structurally related IgSF CAMs CD58 (LFA-3), a cell-surface adhesive ligand with broad tissue distribution. In addition, CD2 can interact with CD48, CD59 and CD15 (Lewis x)-associated carbohydrate structure. CD2 binds CD58 with very low affinity and an extremely fast dissociation constant The lateral redistribution of CD2 and its ligand CD58 also affect cellular adhesion strength. Regulation of CD2 adhesiveness affects the ability of CD2 to enhance antigen responsiveness. CD2-cell lines incapable of avidity regulation exhibit a marked deficiency in an antigen-specific response. Strength of adhesion resulting from increased CD2 avidity contributes directly to T-cell responsiveness independently of CD2-mediated signal transduction.

SUMMARY OF THE INVENTION

The present invention relates to assay methods used for detecting the presence of PIF, and to PIF peptides identified using this assay. In particular, the present invention relates to flow cytometry assays for detecting PIF. It is based, at least in part, on the observation that flow cytometry using fluorescently labeled anti-lymphocyte and anti-platelet antibodies demonstrated an increase in rosette formation in the presence of PIF. It is further based on the observation that flow cytometry demonstrated that monoclonal antibody binding to CD2 decreased in the presence of PIF.

The present invention further relates to PIF peptides which, when added to Jurkat cell cultures, have been observed to either (i) decrease binding of anti-CD2 antibody to Jurkat cells: (ii) increase expression of CD2 in Jurkat cells: or (iii) decrease Jurkat cell viability. In additional embodiments the present invention provides for ELISA assays which detect PIF by determining the effect of a test sample on the binding of anti-CD2 antibody to a CD2 substrate.

BRIEF DESCRIPTION OF THE DRAWINGS

FIG. 2A-C. Western blot analysis of different PIF peptides purified from MECCM; MabCD2 was used as a primary antibody and anti-sense mouse horseradish peroxidase (HRP)-biotin streptavidin complex was used as secondary antibody. Specific PIF bands were identified by the ECL detection reagents (Amersham Pharmacia Biotech).

DETAILED DESCRIPTION OF THE INVENTION

Figure 1:
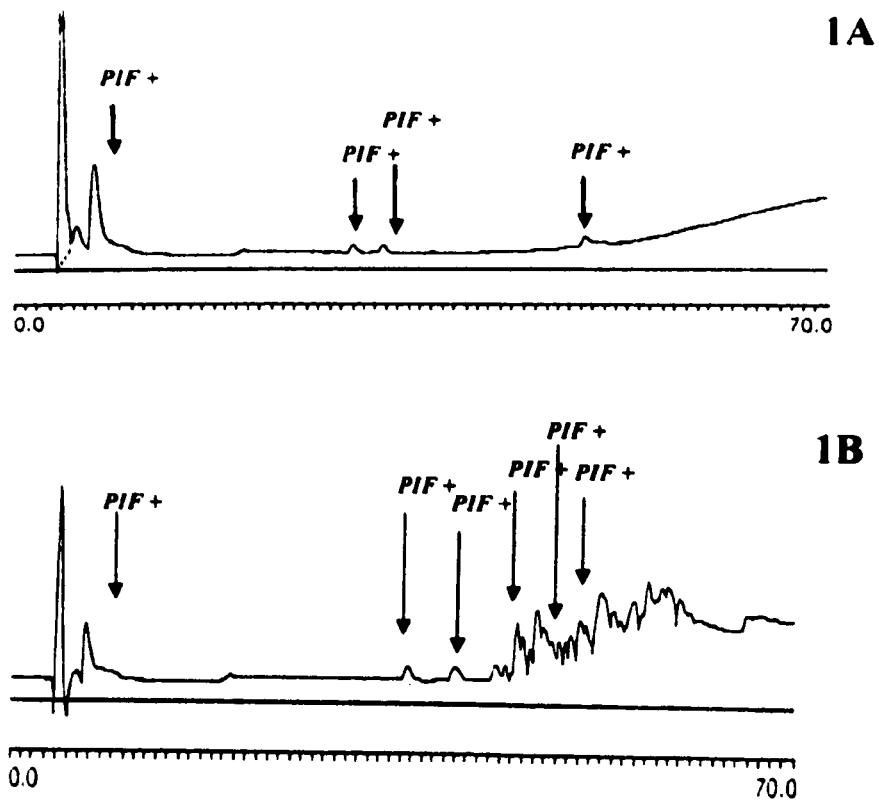
FIG. 1A-B. PIF purification from mouse embryo culture conditioned medium (MECCM); (A) shows a high performance liquid chromatography ("HPLC") profile of MECCM-3 kDA ultra-filtrate previously purified by MabCD2 affinity chromatography; (B) shows the profile following additional HPLC purification of a PIF-active fraction from (A).

In a first set of embodiments, the present invention provides for a method for determining the presence of preimplantation factor in a sample, comprising the step of detecting whether the sample contains a component which inhibits the binding of an anti-CD2 antibody to CD2 antigen; wherein the ability to inhibit the binding of anti-CD2 antibody to CD2 has a positive correlation with the presence of preimplantation factor.

Such a method may, for example, be employed in a flow cytometry method or in an enzyme-linked immunosorbent assay method, using techniques otherwise known in the art. A non-limiting example of a flow cytometry method for detecting anti-CD2 antibody binding to CD2 is presented in Section 7, below.

An anti-CD2 antibody, as that term is used herein, may be a monoclonal or polyclonal antibody which specifically binds to CD2. Such a monoclonal antibody is sold by Pharmigen (see below).

CD2 antigen may be in the form of purified CD2 antigen or may be carried by a cell. In non-limiting embodiments of the invention, the cell is a Jurkat cell. Other CD2-expressing cell lines are known in the art.

The sample may be a serum sample (for example, serum from a subject to be tested for fertilization/implantation/persistence of embryo), may be a sample of culture fluid (for example, to determine the viability of embryos prior to transfer for IVF), or may be a solution to be tested for the presence of a PIF peptide (for example, during the purification of PIF acting agents; see Section 6, below).

The subject may be a human subject (for example, a human suspected of being pregnant) or a non-human subject (for example an agricultural animal or a zoo animal).

In a second set of embodiments the present invention provides for a method for determining the presence of preimplantation factor in a sample, comprising the step of detecting, by flow cytometry, whether the sample contains a component which increases the formation of rosettes between lymphocytes, platelets, and anti-CD2 antibodies, where an increase in rosette formation has a positive correlation with the presence of preimplantation factor. Such an assay may be performed, for example, using fluorescently labeled antibodies directed toward lymphocytes and platelets, where preferably different labels are used for anti-platelet and anti-lymphocyte antibodies.

The increase is relative to a known negative control.

The present invention also provides for the following isolated peptides:

(1) An isolated peptide having a sequence selected from the group consisting of: Met-Val-Arg-Ile-Lys-Pro-Gly-Ser-Ala (SEQ ID NO: 1); Met-Val-Arg-Ile-Lys-Pro-Gly-Ser-Ala-Asn-Lys-Pro-Ser (SEQ ID NO: 2); Met-Val-Arg-Ile-Lys-Tyr-Gly-Ser-Tyr-Asn-Lys-Pro-Ser-Asp (SEQ ID NO: 3); and Met-Val-Arg-Ile-Lys-Pro-Gly-Ser-Ala-Asn-Lys-Pro-Ser-Asp-Asp (SEQ ID NO: 4), or an isolated peptide comprising said peptide which binds to anti-CD2 antibody and which is not a circumsporooite protein;

(2) An isolated peptide having a sequence Ser-Gly-Ile-Val-Ile-Tyr-Gln-Tyr-Met-Asp-Asp-Arg-Tyr-Val-Gly-Ser-Asp-Leu (SEQ ID NO: 5), or an isolated peptide comprising said peptide which binds to anti-CD2 antibody and which is not an HIV protein;

(3) An isolated peptide having a sequence Val-Ile-Ile-Ile-Ala-Gln-Tyr-Met-Asp (SEQ ID NO: 6 or an isolated peptide comprising said peptide which binds to anti-CD2 antibody; and (4) An isolated peptide having a sequence selected from the group consisting of Ser-Gln-Ala-Val-Gln-Glu-His-Ala-Ser-Thr (SEQ ID NO: 7) and Ser-Gln-Ala-Val-Gln-Glu-His-Ala-Ser-Thr-Asn-Xaa-Gly (SEQ ID NO: 8), where Xaa can be any amino acid, or an isolated peptide comprising said peptide which binds to anti-CD2 antibody and which is not a silencing mediator for human retinoid and thyroid hormone.

EXAMPLE

Identification of PIF Peptides

PIF was isolated from a large volume of MECCM using ultra filtration, lyophilization, high performance chromatography (HPLC), affinity chromatography and western blot. Two-cell-to blastocyst stage mouse embryos were cultured for several days in Ham's F-10 medium with penicillin, streptomycin, $MgSO_4$, $NaHCO_3$, $KHCO_3$, and Ca lactate supplemented with 0.1% BSA. MECCM collected was stored at −80° C. until used.

One liter of MECCM was purified by ultra filtration through an Amicon membrane (3 kDa cut-off, YM-3 kDa, Amicon. Millipore Co, USA). Concentrated MECCM was further diafiltered using 300 ml of pure water. In addition, fresh culture media (CM, without embryos) was processed in the same way. Only MECCM-3 kDa ultra filtrate and diafiltrated demonstrated PIF activity and then they were pooled and concentrated by lyophilization.

It was observed that PIF is able to bind to anti-CD2 monoclonal antibody ("MabCD2"). Therefore, PIF-active fractions were purified first by affinity chromatography performed with agarose-hydrazide-MabCD2 activated gels. An antibody affinity matrix was prepared as follows. 1.5 mg of MabCD2 (clone RPA-2.10, Pharmigen, Becton Dickinson) was buffer exchanged with the coupling buffer pH 5.5 using the Econo-Pac 10DG desalting column provided and further oxidized with sodium periodate and coupled to 2 ml of agarose-hydrazide activated gel following the manufacturer's indications (Affi-gel Hidrazide immunoaffinity kit, BioRad Laboratories, CA, USA). Then, MECCM-3 kDa ultra filtrate-diafiltrate lyophilized powder was further purified using the MabCD2-affinity chromatography column (10×20 mm). 2 g of MECCM-3kDa powder were dissolved in 10 ml of pure water, pH neutralized, filter-out through a 0.22 m syringe sterile filter (Corning Inc., NY, USA) and passed 5 times through the affinity chromatography column at gravity flow. The column was washed-out with 5 volume bed of 100 mM phosphate saline buffer, pH 7.2, followed by washing with 5 volume bed of 0.5 M NaCl.

The bound PIF was eluted with 3 ml of 0.1 M acetic acid. PIF-eluted fractions were pooled, assayed for PIF activity and concentrated by lyophilization.

A total of 300 mg of MECCM-3 kDa ultra filtrate further purified by affinity chromatography were run in three batches by HPLC on a Clipeus C18 preparative column (Higgins Analytical, Inc., USA). Preparative HPLC running parameters were: flow, 15 ml/min. Buffers: A=0.1% trifluoroacetic acid (TFA); B=0.1% TFA in 99.9% acetonitrile (CH3CN). Gradient: 0% B, during 5 min plus 0-60% B for 30 min and 0-100% B for 3 min.

Fractions from HPLC were further concentrated by evaporation. HPLC concentrated fractions were pH neutralized and re-assayed for PIF-activity. Several fractions showed high PIF-activity (see FIG. 1A). These fractions were purified by additional HPLC on a Vydac C8 analytical column (4.6×250 mm; Hesperia, Calif., USA). Additional HPLC running parameters: flow, 1 ml/min. Buffers: A=0.1% trifluoroacetic acid (TFA); B=0.1% TFA in 99.9% acetonitrile (CH3CN). Gradient: 0% B, during 5 min plus 0-60% B for 30 min and 0-100% B for 3 min. Several eluted fractions showed PIF activity (see FIG. 1B) and were further sequenced for amino acid composition and their molecular weight (MW) was determined by mass-spectrometry.

PIF active fractions purified from MECCM gave positive signals in Western blots ("WB"). Solutions from CM ultra filtrate-lyophilize fraction was used as negative control in WB. The WB conditions were as follows. For gels, SDS-PAGE pre-casting gels (BioRad) were used, having a 16.5% agarose resolving gel and a 4% agarose stacking gel. The gels were run in 100 mM Tris, 100 mM Tricine, 0.1% SDS, pH 8.3 (Tris-tricine running buffer). Samples consisting of 30 microliters of PIF-MECCM purified fractions plus 10 microliters of Tricine sample buffer [200 mM Tris (hydroxymethyl)aminomethane (Tris-HCl) pH 6.8, 2% sodium duodecyl sulphate (SDS), 40% glycerol, 0.04% Coomassie blue brilliant (CBB-G250)] (BioRad) were incubated at 95° C. during 5 min. After cooling, the samples were loaded into the wells of the SDS-polyacrylamide gels (PAGE). To determine the molecular weight of low molecular weight (MW) polypeptides, 10 microliters of a 1:20 water dilution of SDS-PAGE standards (BioRad) were loaded into a well of each gel. For electrophoresis, samples and standards were run at 175 v during 5 min plus 60 v for 1 h.

The resulting gels were then electro-blotted using, as transfer buffer, 100 mM CAPS [3-(cyclohexylamino)-1-propanesulfonic acid] buffer, pH 11. Electro-blotting was performed at 80 mA during 1 h onto a 0.22 μm nitrocellulose membrane (BioRad).

Then, nitrocellulose membranes were blocked with 5% blocking solutions (Amersham. Pharmacia, Biotech, NJ, USA) at room temperature during 18 h., and then were washed-out 4 times during 20 min with PBS-T [phosphate saline buffer −0.05% polyoxyethylenesorbitan monolaurate (Tween 20)]. For the primary antibody incubation, blocked membranes were incubated with 2 μg/ml MabCD2 (Pharmigen)—PBS-T solutions at room temperature during 2 h, and then washed as above. For the secondary antibody incubation, the membranes were incubated with anti mouse IgG-horse radish peroxidase conjugate (1:1000 in PBS-T) solution at room temperature during 1 h. PIF bands were then visualized using the ECL-chemiluminescent system (Amersham). FIG. 2 shows a typical WB of PIF peptides purified from MECCM.

Figure 3A:
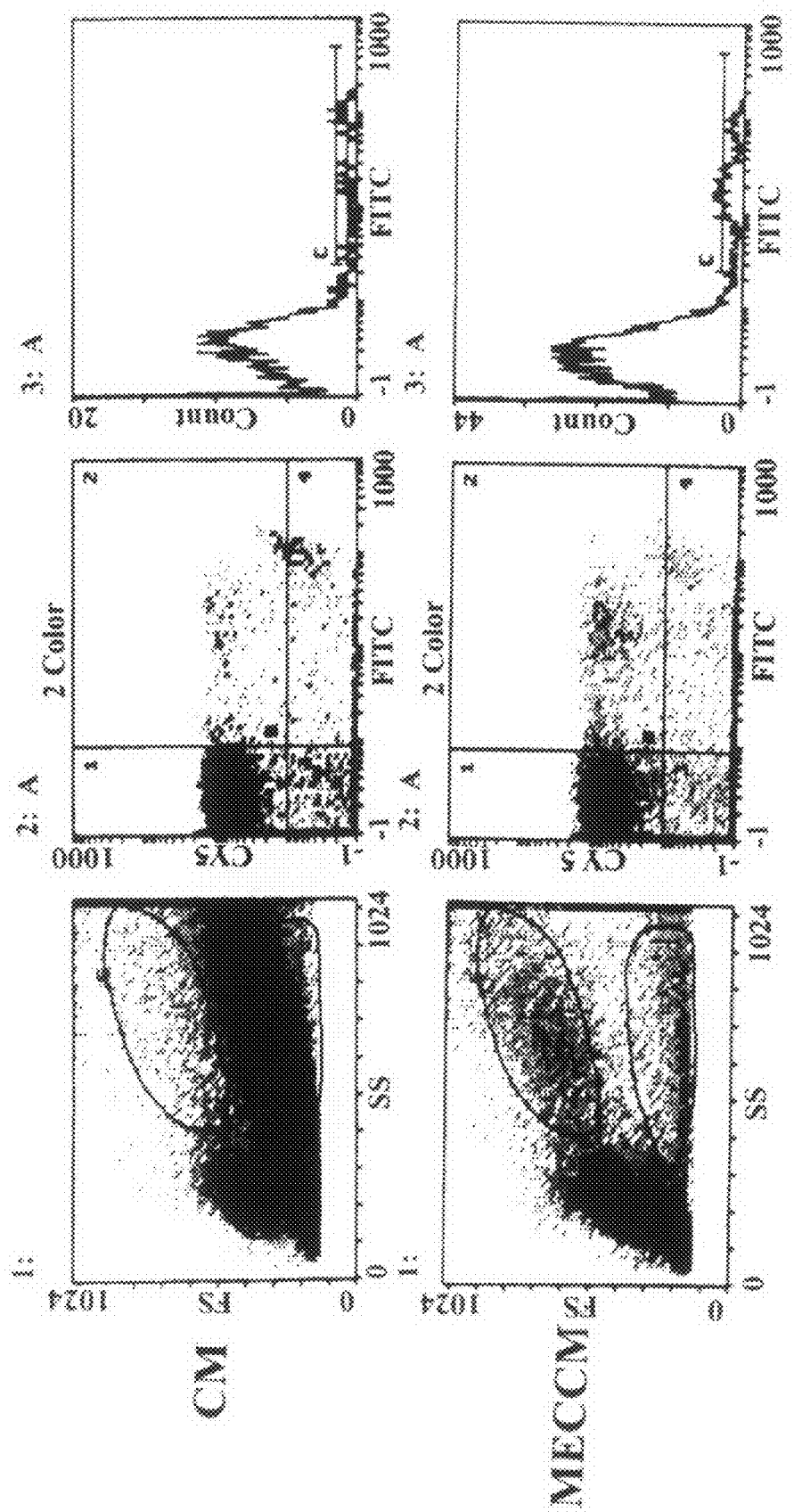
FIG. 3A-B. (A) shows flow cytometric determination of lymphocyte-platelet rosette formation (L-P) in the presence of fresh culture medium (CM) and mouse embryo culture conditioned medium (MECCM) and MabCD2. Fluorescent labeled specific antibodies to L (MabCD45-PE) and to P (MabCD42a-FITC) were used to detect the L-P complex. MECCM gave 3Q-40 percent higher formation of L-P compared to culture medium (CM). (B) shows FC of MECCM effect on MabCD2 binding to Jurkat cells (JC). JC were incubated with samples and further with MabCD2 Cy5. Antibody binding to CD2 decreased by PIF present in MECCM. Arrows indicate PIF activity.

A flow cytometric methodology (FC) for measuring PIF was developed to improve the efficiency and reproducibility of methods set forth in U.S. Pat. Nos. 5,646,003 and 5,981, 198. In particular, rosette formation was evaluated by FC with pregnant and non-pregnant human and porcine serum, MECCM, CM and isolated PIF-fractions using MabCD2 or MabCD2-Cy5 (Cy-chrome conjugated antibody), MabCD45-PE (phycoerytrhin conjugated antibody) and MabCD41a-FITC (fluorescein isothiocyanate conjugated antibody), all antibodies were from Pharmigen. The ratio of labeled P-L complex was higher by 30-40% with MECCM versus CM (FIG. 3A). Further, it was found that pre-incubation of MECCM or pregnant sera with immobilized MabCD2 prevented the P-L formation in the assay. The addition of a MabCD58 (lymphocyte function-associate antigen-3 or LFA-3) antibody to L-P did not prevent totally the rosette formation by effect of PIF-active samples in the assay.

Figure 3B:
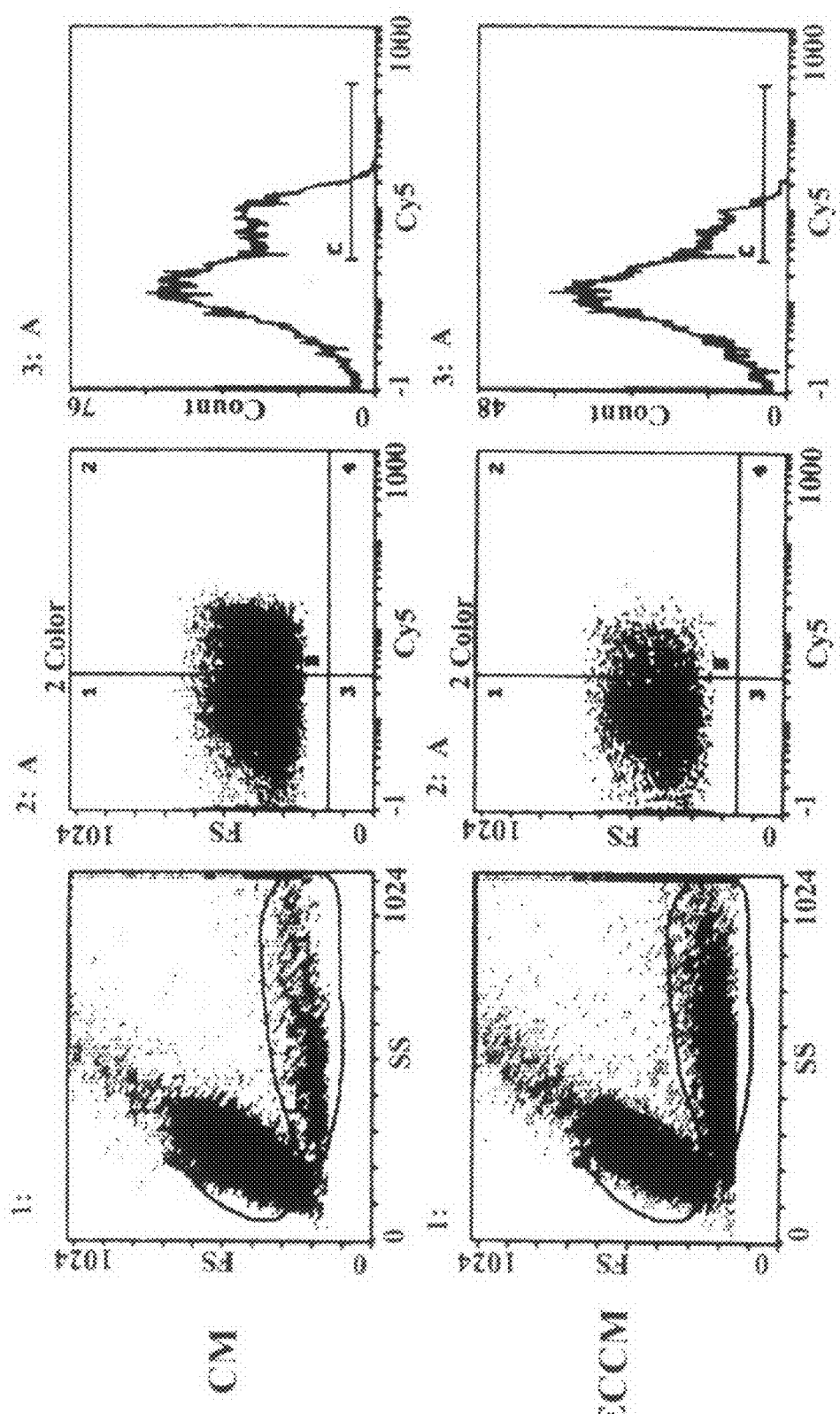

A FC-PIF quantitative assay using Jurkat cells (JC) and MabCD2-Cy5 was developed (FIG. 3B). The use of an immortalized leukemia cell line avoids the need for fresh donor blood to assess the PIF activity by the bioassay. The JC-FC assay was validated with human serum samples (see Table I) and was used to assess PIF activity of fractions during PIF purification.

Figure 4A:
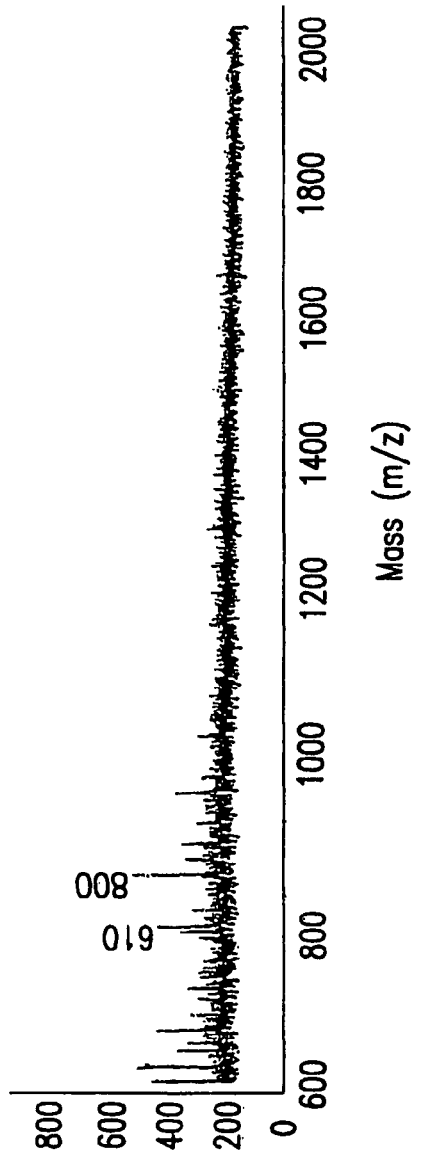
FIG. 4A-C. Mass spectrum from PIF peptides purified from MECCM. Molecular weight (MW) of PIF-active fractions from MECCM purified by ultrafiltration, diafiltration, HPLC, MabCD2-affinity chromatography and by additional HPLC was determined by mass spectroscopy. MW of PIF peptides were A) 610-995 Da; B) 963-1848 Da; and C) 1807-1846 Da.
Figure 4B:
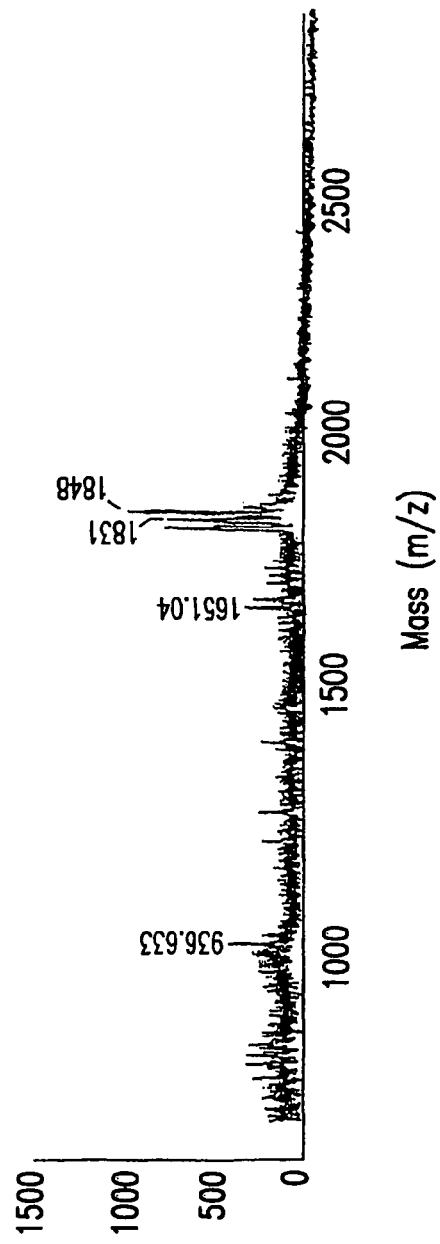
Figure 4C:
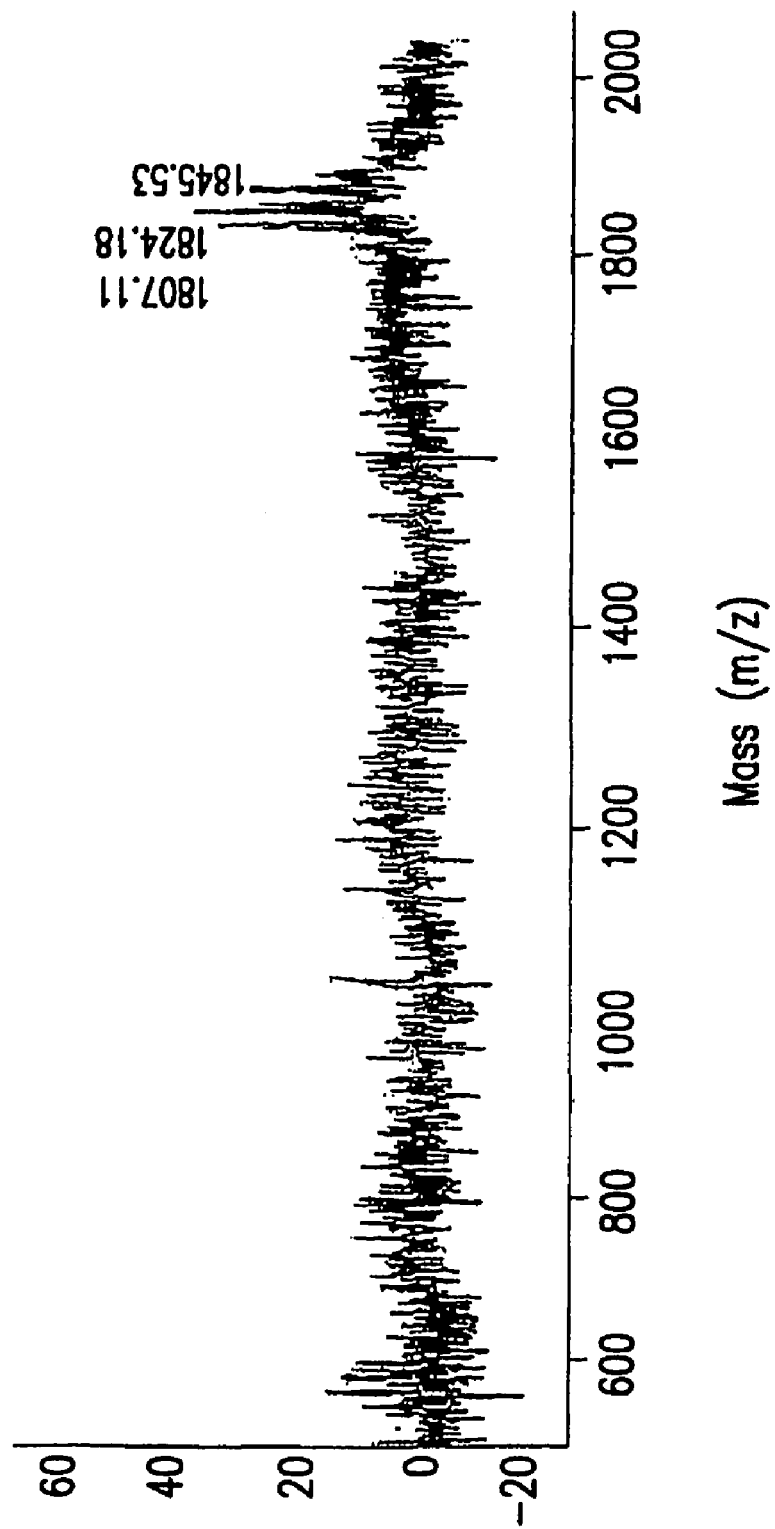

MW of purified PIF-active fractions was determined by mass spectral analysis on a Voyager-RP Biospectrometry MALDI-TOF Workstation from Perseptive Biosystems (Cambrigde, Mass., USA). Samples were mixed with a matrix consisting in a 1:2 mixture of acetonitrile:water containing 1% trifluoroacetic acid. Spectra were averages of approximately 200 scans. PIF-peptides from MECCM have MW between 610-1845 Da (FIG. 4).

Further, it was assessed that pre-incubation of PIF-active fractions with MabCD2 abolished the PIF-activity. These data indicated that PIF could be a portion of CD2 or homologue peptides. However, after the sequencing of purified PIF peptides it was demonstrated that these peptides are not a portion of CD2 and their amino acid sequences are unique.

Using the JC-FC assay it was demonstrated that MEECM-PIF peptides have three different effects on CD2 expressed by T cells. These effects are related to:

decreasing MabCD2 binding to the JC; up-regulating CD2 expression by JC; or decreasing JC viability.

Purified PIF active fractions from mouse embryos were sequenced by Edman degradation on an Applied Biosystems Pulsed Liquid Sequencer (model 477A). Released amino acids were derivatized with phenylisothiocyanate to give the PTH-amino acids which were detected by reverse phase-HPLC on a HPLC system in line with the sequencer. Several of the PIF fractions yielded unique sequences. Several peptides gave sequences whose N-terminal nine and ten residues were identical indicating that the peptides were various truncated forms of common molecules (see Table II). PIE peptides were identified as a least three unique families of embryo-derived and pregnancy-related small peptides. The amino acid sequence of a family of three PIF peptides matches 100% with a region of Circumsporozoite protein (malaria parasite: Plasmodium falciparum) (SEQ ID Nos. 1, 2 and 4). This family of PIE peptides up regulates the CD2 expression by JC. A PIF peptide (14 amino acids) (SEQ ID No. 3) that shares only the five first amino acid residues with the former described PIF-peptide's family and another PIE peptide (18 amino acids) (SEQ ID No. 5) that matches in 11 amino acids to the sequence of HIV-1 RNA directed DNA polymerase (reverse transcriptase, EC 2.7.7.49) also up regulate the CD2 expression by JC. In addition, another family of two PIT peptides (10 and 13 amino acids) (SEQ ID No. 7 and 8) matches in 10 amino acids with the sequence of the human receptor-interacting factor, a silencing mediator for retinoid and thyroid hormone receptor (SMRT) (Chen and Evans, 1995). The shorter member of this PIE-peptide family shows a competitive effect for the binding of MabCD2 to JC and the longer PIF-peptide decrease the viability of JC. It is worth to notice that transcriptional silencing mediated by nuclear receptors is important in development, differentiation and oncogenesis.

Figure 6:
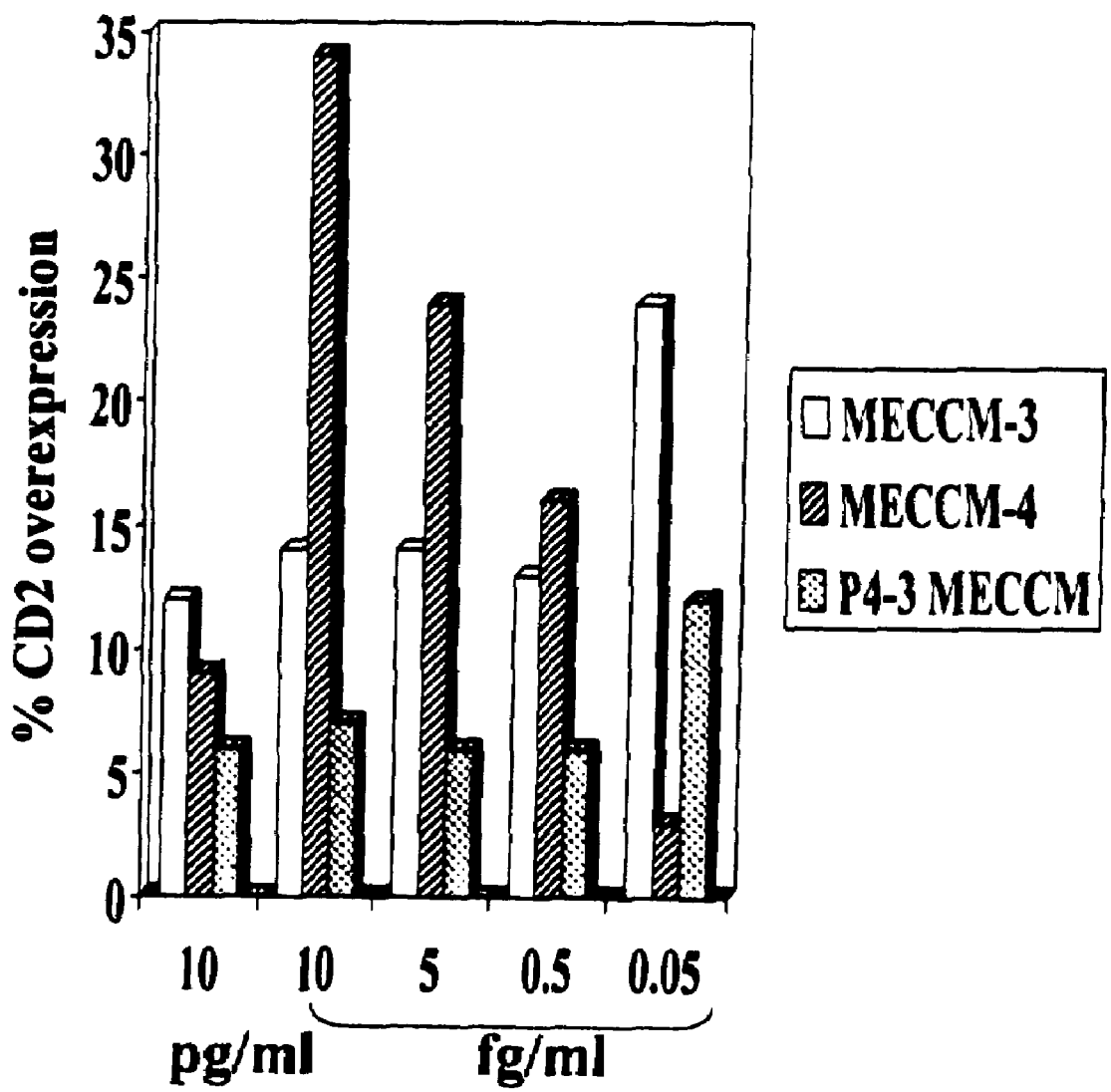
FIG. 6. Effect of Synthetic PIF peptides on CD2 expression on Jurkat cells.

PIF peptides were synthesized by solid-phase peptide synthesis (SPPS) on an Applied Biosystems Peptide Synthesizer employing Fmoc (9-fluorenylmethoxycarbonyl) chemistry in which the amino nitrogen of each amino acid is blocked with Fmoc. Coupling was performed by activation of the carboxyl groups of the N-protected amino acids using 3 mmol/ml of 2-(1H-benzotriazol-1-yl)-1,1,3,3-tetramethyluronium tetrafluoroborate/1-hydroxybenzotriazole on the presence of diisopropylethylamine. Activated amino acids were sequentially added to the nascent peptide. Upon completion of the synthesis, final purification was carried out by reversed-phase HPLC and identity was verified by MALDI-TOF mass spectrometry and amino acid analysis. PIF synthetic peptides demonstrated to have similar effect on CD2 phenomenon in Jurkat cells (FIG. 6), and were also immunodetected by the Mab CD2.

Flow Cytometry Assay for PIF Materials

Materials included Jurkat leukemia cells (JC); cloning medium; Falcon tubes for flow cytometry measurements; Mab CD2-Cy5 (Cy-chrome conjugated antibody, clone RPA-2.10, Pharmigen, Becton Dickinson); the biological sample (which could be a human serum to be assayed for PIF activity, or could be a solution of a putative or synthetic PIF peptide); PBS-2% BSA (100 mM phosphate saline buffer −2% bovine serum albumin; a negative control); trypan-blue dye; a $CO_2$-incubator for cell culture; and a flow cytometer.

Method

To Prepare the JC Suspension:

Check the viability of the JC culture using Trypan blue dye exclusion staining. Cell viability should be between 80-90%.

Wash twice the JC with 10 ml of PBS-2% BSA.

Prepare a JC suspension in cloning medium or PBS-2% BSA containing 5,000,000 cells/ml.

Dispense 50 ml of JC suspension into falcon tubes (250,000 cells/tube).

For the Sample Incubation:

Add 200 ul samples, serum from early pregnancy controls (3 positive controls) or PBS-2% BSA (negative control). Mix gently.

Incubate at room temperature for 20-30 min.

Add 200 ul of MabCD2-Cy5 diluted 1:200 in PBS-2% BSA. Mix gently.

Incubate at room temperature for 20-30 min.

Figure 5:
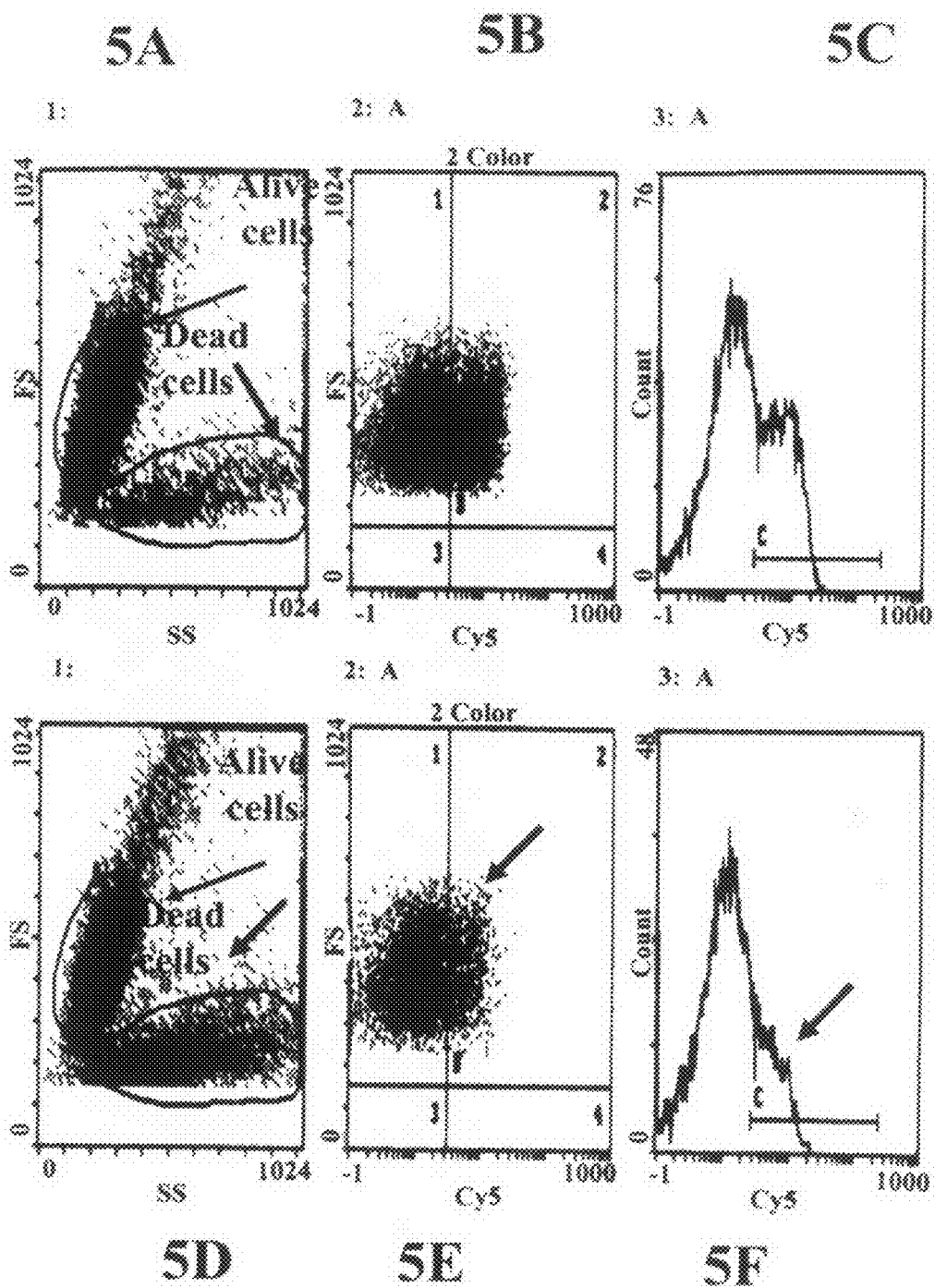
FIG. 5A-F. Flow cytometric analysis of PIF negative effects on MabCD2 binding (A), fluorescence (B) and viability (C) in Jurkat cells, and of PIF positive effects on MabCD2 binding (D), fluorescence (E) and viability (F). PIF in positive samples competes with CD2 (arrows indicate PIF activity).

For Flow Cytometric Determination:

Measure the fluorescence of each tube (488 nm laser excitation wavelength). Compare the fluorescence of alive and total cells and total dead cells (see FIG. 5) with controls.

Calculate PIF Activity as Follows:

Fluorescence of total cells/% dead cells×Fluorescence of alive cells

Interpretation of the Results

PIF negative activity should be in the range of: 130-340

Positive PIF samples are out side of the negative reference range

Various publications are cited herein, the contents of which are hereby incorporated by reference in their entireties.

TABLE I

CLINICAL VALIDATION OF THE FLOW CYTOMETRIC PIF ASSAY IN SERUM FROM 37 PATIENTS

| Samples | Sensitivity (%) | Specificity (%) | Positive predictive Value (%) | Negative predictive Value (%) |
|---|---|---|---|---|
| Early pregnancy | 91 | 92 | 92 | 92 |
| Mid pregnancy | 66 | 92 | 86 | 73 |
| Late Pregnancy | 100 | 92 | 83 | 92 |
| All pregnant Samples | 86 | 92 | 88 | 86 |

TABLE II

Amino acid sequence of PIF peptides derived from pre-implantation mouse embryos

| PEPTIDE CODE/ AMINO ACID NUMBER | SEQUENCE | T CELL RELATED CD2 ACTIVITY | SEQUENCE MATCHING (REFERENCE) |
|---|---|---|---|
| MECCM-4 (9 AA) | [H]-m-v-r-i-k-p-g-s-a[OH] (SEQ ID NO: 1) | Increase of CD2 expression | Match 100% in 9 AA with circumsporooite protein (malaria parasite-*Plasmodium falciparus*) |
| MECCM-6 (13 AA) | [H]-m-v-r-i-k-p-g-s-a-n-k-p-s-[OH] (SEQ ID NO: 2) | Increase of CD2 expression | Match 100% in 9 AA with circumsporooite protein (malaria parasite-*Plasmodium falciparus*) |
| MECCM-3 (15 AA) | [H]-m-v-r-i-k-p-g-s-a-n-k-p-s-d-d-[OH] (SEQ ID NO. 4) | Increase of CD2 expression | Match 100% in 9 AA with circumsporooite protein (malaria parasite-*Plasmodium falciparus*) |
| MECCM-5 (14 AA) | [H]-m-v-r-i-k-y-g-s-y-n-k-p-s-d-[OH] (SEQ ID NO: 3) | Increase of CD2 expression | Match 100% in SAA with circumnsporooite protein (malaria parasite-*Plasmodium falciparus*) |
| MECCM-7 (18 AA) | [H]-s-g-i-v-i-y-q-y-m-d-d-r-y-v-g-s-d-l-OH] (SEQ ID NO. 5) | Increase of CD2 expression | Match 100% in 11 AA with HIV-RNA-DNA directed polymerase (EC 2.7.7.49) |
| P 14-6 (9 AA) | [H]-v-i-i-i-a-q-y-m-d-[OH] (SEQ ID NO: 6) | Competition with MabCD2 for binding | No match |
| P13-5 (10 AA) | [H]-s-q-a-v-q-e-h-a-s-t-OH] (SEQ ID NO: 7) | Decrease of cell viability | Match 100% in 10 AA with a silencing mediator for human retinoid and thyroid hormone receptor (SMRT) |
| P4-3 (13 AA) | [H]-s-q-a-v-q-e-h-a-s-t-n-a-g-OH] (SEQ ID NO: 8) | Decrease of cell viability | Match 100% in 10 AA with a silencing mediator for human retinoid and thyroid hormone receptor (SMRT) |

The invention claimed is:

1. An isolated peptide which binds to anti-CD2 antibody, said isolated peptide comprising the sequence Ser-Gly-Ile-Val-Ile-Tyr-Gln-Tyr-Met-Asp-Asp-Arg-Tyr-Val-Gly-Ser-Asp-Leu (SEQ ID No: 5).

* * * * *